(12) United States Patent
Detwiler et al.

(10) Patent No.: US 7,458,741 B2
(45) Date of Patent: *Dec. 2, 2008

(54) MULTIPLE COMPARTMENT STORAGE AND DISPENSING APPARATUS

(75) Inventors: Bruce D. Detwiler, Boyertown, PA (US); Dennis H. Chadwick, Ottsville, PA (US)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 480 days.

This patent is subject to a terminal disclaimer.

(21) Appl. No.: 10/825,016

(22) Filed: Apr. 15, 2004

(65) Prior Publication Data

US 2004/0223801 A1 Nov. 11, 2004

Related U.S. Application Data

(63) Continuation-in-part of application No. 10/431,769, filed on May 8, 2003, now Pat. No. 6,902,335.

(51) Int. Cl.
*B43K 5/14* (2006.01)
*B43K 5/00* (2006.01)
*B43K 5/02* (2006.01)

(52) U.S. Cl. .................... 401/132; 401/205; 401/40

(58) Field of Classification Search ......... 401/132–135, 401/196, 205, 202, 40; 604/1–3; 222/145.5
See application file for complete search history.

(56) References Cited

U.S. PATENT DOCUMENTS

| | | | |
|---|---|---|---|
| 4,812,067 A * | 3/1989 | Brown et al. ................. | 401/132 |
| 5,242,433 A * | 9/1993 | Smith et al. ................. | 604/289 |
| 5,558,874 A * | 9/1996 | Haber et al. ................. | 424/402 |
| 6,547,468 B2 * | 4/2003 | Gruenbacher et al. ....... | 401/133 |

* cited by examiner

*Primary Examiner*—David J. Walczak
(74) *Attorney, Agent, or Firm*—Fitzpatrick, Cella, Harper & Scinto

(57) ABSTRACT

A storage and dispensing apparatus designed to contain pre-measured amounts of a substance(s). The apparatus comprises at least one compartment, preferably at least two compartments, for storing the substance(s) that is partially enclosed by a frangible seal, an applicator or dispensing conduit, and an expandable chamber designed to accept and dissipate the hydraulic force created when pressure is applied to the at least one compartment rupturing the frangible seal, and expelling the substance(s) into the chamber. The applicator is attached to the chamber with an applicator bond area. The expandability of the chamber is conferred by expandability of the chamber walls and of the applicator, when present, and is varied in different embodiments by altering the ratio between the area of the applicator bond area and the area of the applicator. The frangible seal, in one of many embodiments, may be a chevron shape stress riser with a point of inflection oriented towards the compartment. A removable cap may cover the applicator or dispensing conduit.

32 Claims, 11 Drawing Sheets

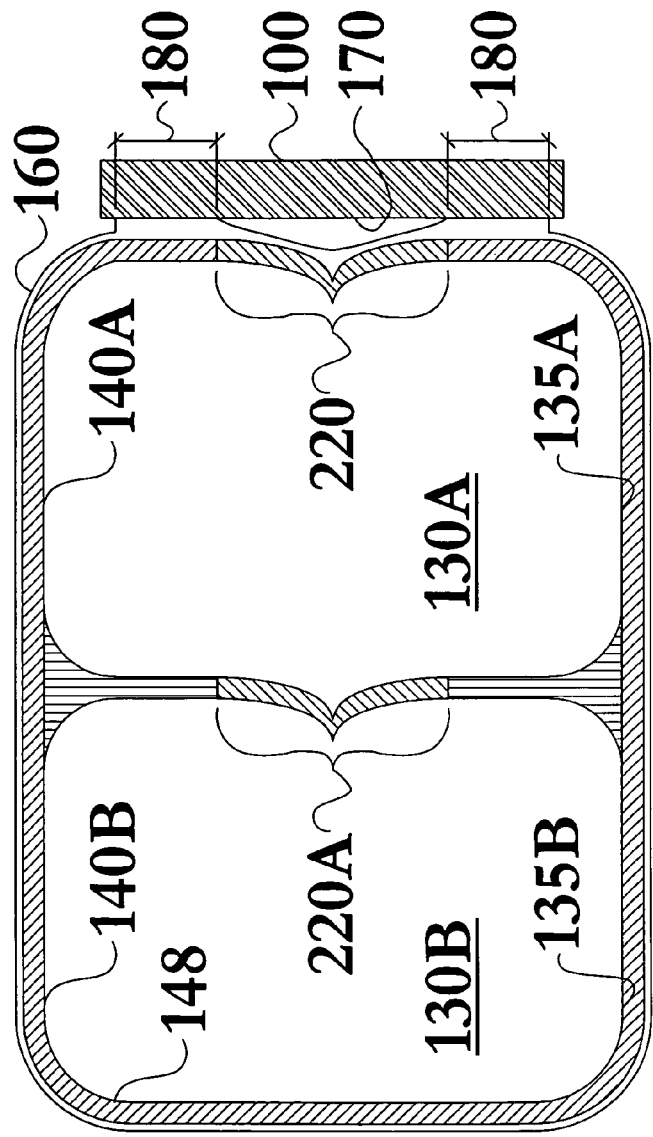
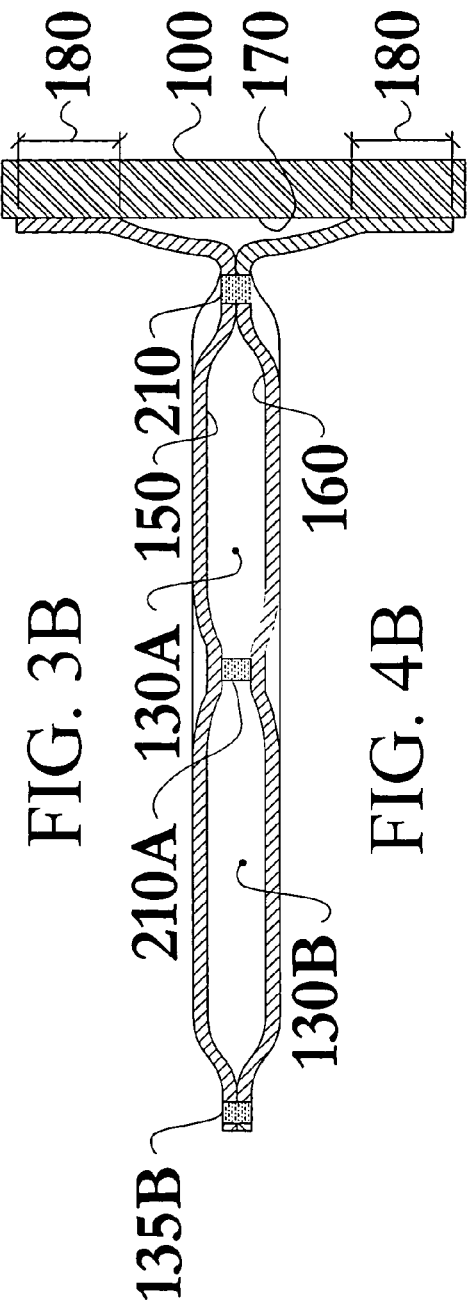
FIG. 3B
FIG. 4B

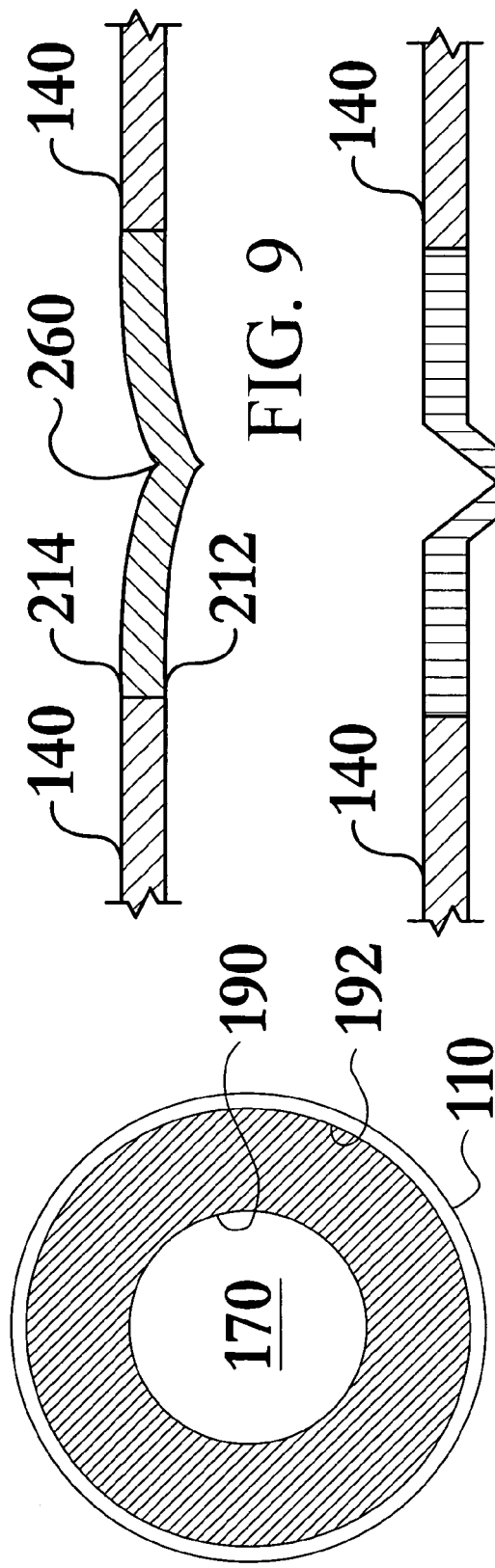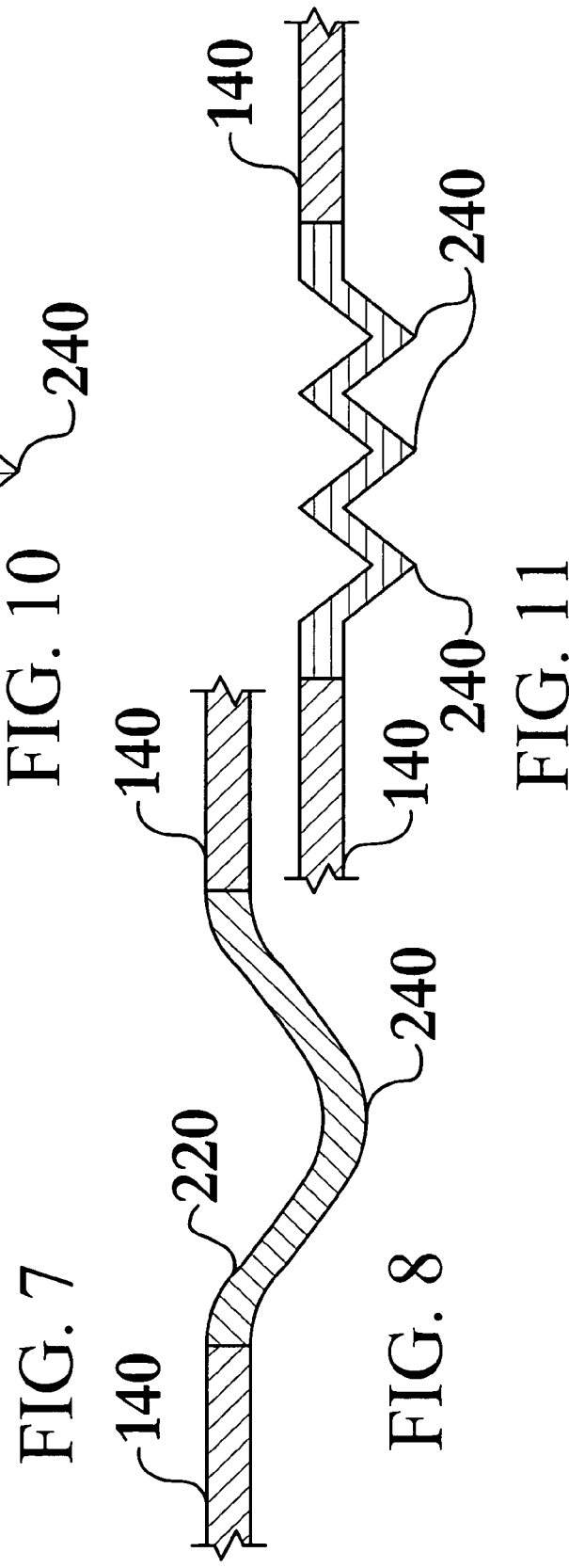

MULTIPLE COMPARTMENT STORAGE AND DISPENSING APPARATUS

REFERENCE TO RELATED DOCUMENTS

This application is a continuation-in-part of a previous application filed in the United States Patent and Trademark Office by Jim Hussey and Michael S. Bergey on May 8, 2003, titled "Dispensing and Application Apparatus," Ser. No. 10/431,769 now U.S. Pat. No. 6,902,335.

TECHNICAL FIELD

The instant invention relates to hand held dispensing packages, and particularly to a flexible package for storing and dispensing substances, that may be mixed prior to dispensing. The inventive package has at least one controlled rupture seal feature that is in communication with a dispensing conduit that provides for an even distribution of the substance onto an integral absorbent pad. The integral absorbent pad facilitates a clean and even spreading of the dispensed substance.

BACKGROUND OF THE INVENTION

Measured amounts of various fluid substances, flowable dry products, and solid substances are increasingly commonly dispensed in relatively small flexible packages often composed of plastic or foil. The substances and products include a wide variety of products, including foodstuffs such as condiments, personal care products such as shampoos, cleaning products such as packaged "wipes," and pharmaceutical products such as medications.

A typical example is that of the ubiquitous single serving ketchup pack, which is generally formed of two sheets of foil or plastic, superimposed over one another and then sealed together around the periphery, with a notch or other means to facilitate tearing one edge away from the container. The user tears open the container dispenses the condiment, and then disposes of the package. Similar single unit, single dose containers are also often used to house dry flowable products, such as salt and solid substances, such as pills and medications.

Such packaging, while relatively simple and inexpensive, poses numerous drawbacks in this most simple embodiment. Firstly, the simplest such package contains no integral means for directing or spreading the dispensed fluid. In particular, thick fluids tend to be dispensed as a bolus, leaving the user to find an implement to spread the bolus, or otherwise to improvise with the possibly unsanitary outside of the now empty package to form a crude spreader. Alternatively, thin fluids tend to be dispensed in a difficult to control stream.

Second, the package can be quite difficult to open, particularly for those with arthritic hands or otherwise weakened grip strength. This difficulty is at least in part caused by the fact that, in the simplest conventional embodiments of this package, it is necessary to tear away one of the sidewalls of the packaging in order to release the contents. Such a sidewall must be relatively strong in order to contain the contents under normal handling conditions, which may include accidental compression. Even a small amount of moisture or skin oil on the surface of the packaging can make gripping and tearing the generally small package nearly impossible. It is extremely common to see frustrated users of such packaging using their teeth to open ostensibly manually "tear open" packages. Such a technique poses obvious aesthetic and hygienic issues.

Third, velocity of the product as it is expelled from the packaging varies immensely with the characteristics of the product, the relative amount of side wall opened, and the pressure, which is applied to expel the contents. Anyone who has squeezed a ketchup package with only a pinpoint opening in its side can testify to the extreme distances the condiment can be propelled, often onto clothing, furniture, or even other persons.

Fourth, prior packaging has lacked the ability to efficiently and separately house products or substances that are to be mixed together just prior to administration.

Various attempts have been made over the years to address these problems, with varying degrees of success. The creation of packaged, pre-moistened towelettes, facilitates spreading but requires a handling of the dispensed contents. Pre-loaded, disposable, swabs obviate handling, but contain very small amounts of dispensable liquid. As to the problem of spreading more than a minimal amount of liquid without handling the liquid, for example, the need to facilitate spreading a dispensed liquid was addressed by means of an integral roller in U.S. Pat. No. 5,577,851 to Koptis. The '851 patent teaches a sponge applicator attached to a tube dispenser that contains multiple unit quantities of a substance, such as painter's spackle, to be dispensed. After use, the sponge applicator is designed to be removed, cleaned, and returned to the tube dispenser. The reuse of the sponge applicator raises the issues of potential hardening and chemical or bacterial deterioration of residual product in the sponge and therefore the dispensing of contaminated product upon the container's next use. This makes it unsuitable for use with products such as those intended for human consumption, where bacterial contamination may be devastating. Such sensitive products can be protected with single use, or "throw away" sponge applicators, but the complexity of the '851 device makes it ineffective on a cost basis for single use containers.

A similar attempt to provide an integral spreader is seen in U.S. Pat. No. D363,377, which provides a roller atop a dispensing container. The roller spreads the dispensed fluid, but is subject to the same cleaning and hygienic drawbacks posed by the sponge pad applicator of the '264 patent.

Efforts to simplify an integral spreading means to make designs suitable for single use containers have exhibited mixed success. For example, U.S. Pat. No. 6,007,264 to Koptis teaches a variation on the simplest form of packaging, that of two superimposed sheets sealed together around their periphery, with the provision of peelable flaps along one edge of the package. The user peels back the flaps, pulling apart one sealed edge of the package and thus exposing the contents. The peeled back flaps, at an approximate 90-degree angle to the package, thereby provide a butterfly wing type spreader for spreading the contents. Such a design obviates any need to clean or re-use the spreading device, as the entire unit is disposable.

However, the utility of the '264 design has been found to be directly proportional to the viscosity of the fluid dispensed. For example, fluids with a high viscosity, such as ketchup or heavy creams, tend to be dispensed as the design envisions, as a discrete bolus, whereupon they can be effectively smeared about the intended surface by the butterfly wings. However, experimentation has shown that liquids of low viscosity, such as some pharmaceutical preparations and other relatively thin liquids, tend to be dispensed from the opened container in a stream, as opposed to a bolus, and run out of the flap or wing spreading area before they can be effectively spread.

The '264 device attempts to counter this propensity by disclosing an embodiment wherein an absorbent pad either is applied in two pieces to the opposing flaps or is applied in a single piece bridging the flaps. Such structures are designed to provide an absorbent surface area to facilitate the spreading of the dispensed fluid. However, experimentation with the design has revealed that it is marginally, at best, effective for this purposed. In practice, separate pads that do not bridge the container opening may increase absorbency for spreading, but do nothing to retard the sudden flow of material from the ruptured packaging. Even in the embodiment wherein the absorbent pad bridges the opening, practice has shown that when the pouch is squeezed and the frangible seal under the absorbent pad breaks, the contents of the pouch burst through the seal and the liquid tends to squirt through the absorbent pad, rather than being gently absorbed into the pad as intended.

As to the second problem, that of facilitating the opening of the container, various methods have been proposed. The '264 device, discussed above, provides enlarged tear flaps that are intended to facilitate gripping the container, however, the problem of tearing the relatively strong sidewall of the container still remains.

In U.S. Pat. No. 4,921,137 to Heijenga, the container is equipped with an enlarged ear-like structure that facilitates grip. In addition, the '137 device contains, within the ear-like structure, a preformed channel portion that attempts to address the third problem, that of dependably producing a large enough egress channel for the dispensed material so as to minimize excessive pressure effects, such as uncontrolled squirting of the contents. However, the '137 device makes no provision to address the first problem, that of spreading a bolus of dispensed liquid.

Additional problems are raised with substances that are ideally mixed just prior to use, and the art has long sought an effective means of storing, mixing, and dispensing such substances. In U.S. Pat. No. 5,330,048 to Haber, et al., teaches a controlled access mixing vial with a mixing and a supplemental container. Collapsing the mixing and supplemental containers is accomplished by means of turning a rotary threaded coupling, which causes a breachable seal to rupture, and then the mixing of the contents of the two containers. Such a device suffers from the inherent mechanical complexity of its design. A mechanically simpler design is seen in U.S. Pat. No. 6,059,443 to Casey. In the '443 device, a mixing container holds a smaller storage container suspended at an egress end, where it is closed off from the mixing container by a seal. If the seal is removed and a specially configured cap is placed over the egress end, agitation of the mixing container will cause the contents of the storage container to be shaken into the mixing container. While this device is inherently simpler, it lacks the closed nature of the more complex '048 device.

What has been needed, and heretofore unavailable, is a disposable, unit dose container for storing and dispensing fluid substances, flowable dry products, and/or solid substances that allows for easy opening and potential mixing and application of the contents without physically touching the contents. Such a storage and dispensing pouch must be inexpensive and easy to manufacture, maintain the integrity of the contents until dispensing, and must reliably dispense the contents without being unduly susceptible to accidental release, yet be easily susceptible to intended opening by the user, who may include persons of limited strength, coordination, or sight. One particular embodiment may incorporate an absorbent pad capable of protection by a sterility enhancing cover that can be easily removed just prior to dispensing. The design of the pad facilitates easy and even spreading of the container contents, with the absorbent pad being soft and comfortable in applications involving spreading of liquid upon the skin.

SUMMARY OF THE INVENTION

The instant invention provides a novel dispensing apparatus, mixing apparatus, and application apparatus that addresses the shortcomings of the prior art. In its most general design, the apparatus comprises at least one compartment, a chamber, and a plurality of seals. The chamber and the compartment, which may be fabricated out of separate structures that are later joined, is, in the preferred embodiment, fabricated as a single structure separated into two sections by a frangible seal.

The apparatus is designed to contain fluid substances, flowable dry products, and/or solid substances until the point of dispensing, at which point pressure upon the compartment area, where the substance(s) is stored, ruptures the frangible seal and expresses the substance into the chamber or an adjacent compartment. The expansion of the chamber walls and the resilience of the applicator pad, when present, help dissipate the energy of the substance as it breaks through the frangible seal, thereby ensuring a controlled release.

The prior art describes the concept of an applicator attached to flexible foil wings of a dispensing package, but experimentation with such a design revealed that it was unsuitable in any number of applications. When sufficient pressure is exerted behind a seal of a closed compartment, the seal ruptures and the material behind the seal is expelled through the ruptured seal. The force with which the material flows through the ruptured seal depends on a multiplicity of factors, including but not limited to the viscosity of the fluid, the amount of pressure applied, and the orifice area, of the rupture in the seal.

Experimentation with the general design of the package of U.S. Pat. No. 6,007,264 to Koptis, while sufficient in some applications, showed a number of shortcomings. First, if the applicator pad were attached as separate pads and opposing pads disposed on the underside of the outwardly folding wings, there was an observed tendency for the dispensed substance to break through the frangible seal and squirt out on the user, floor, or otherwise unsuitable direction, before it could be absorbed and spread by the absorbent pads. It was noted that the severity of this problem increased with increased pressure, decreased area or orifice of seal rupture, and decreased viscosity of the substance dispensed. Alternatively, when the absorbent pad was designed as a single pad spanning the central opening in the packaging seal, the problem remained unattenuated, as the dispensed substance tended to shoot through the absorbent pad, with the same ill effects noted above.

In contrast, the instant invention, among other advantages, achieves controlled dispensing and application by the combination of two essential features. First, it has a controlled rupture seal that reliably ruptures at a predetermined pressure with a sufficient orifice size, to prevent extremely high velocity dispensing. Second, the apparatus features an expansion chamber that absorbs the hydraulic shock of the expelled substance.

Experimentation with various designs of frangible seals revealed that some designs achieved at least a degree of success. For example, the frangible seal could be a straight frangible seal fabricated to be thinner, or to be less securely heat sealed, than the primary seal. A second design, a frangible seal with a stress riser oriented away from the pressure, is possible. However, in the preferred embodiment, a frangible seal with a chevron shape stress riser with the point of maximum inflection oriented towards the pressure, as is described in detail below, was found to present optimal characteristics in terms of breaking reliability and adequate seal rupture area.

Even with an optimally designed frangible seal, it was realized that an expansion chamber was needed to contain the dispensed substance at a reasonably low pressure while it was being absorbed into the applicator. It was found that a chamber wherein one side comprised a flexible foam or otherwise absorbent pad imparted sufficient expandability to absorb the hydraulic shock of the dispensed substance breaking through the frangible seal. However, it was also observed that the sizing of the chamber played an important role in the efficacy of the chamber concept. If the applicator pad were attached over a relatively large area to the walls of the package, there would be relatively little expansive wall available to cushion the aforementioned hydraulic shock, and the substance would demonstrate the squirt through problem observed earlier. At least theoretically, if the applicator pad were attached over a very small area of the walls of the package, there would be a relatively large expansive wall available to cushion the hydraulic force, and there might be insufficient force to move the substance into and through the applicator pad. Additionally, the apparatus advances the art by providing for a removable cap for either the applicator pad or dispensing conduit, depending on the embodiment, which can maintain cleanliness, or even sterility, of the applicator pad or dispensing conduit.

The apparatus offers a low cost disposable packaging for a wide array of substances, which can include, by way of example and not limitation; pharmaceutical antiseptics, salves, ointments, creams, powders, solutions, and multi-part solutions. Additionally, the present invention provides a package that offers convenience in storage, resistance to package breakage, better sanitation, and lower spillage or waste. In addition, this invention provides a package that allows a user to apply a small measured quantity of a substance in a controlled manner without getting it on the fingers or hands and without the necessity of using the fingers, hands or an additional implement to spread the substance. The ability to easily apply the dispensed substance without direct hand contact with the substance relieves aesthetic and hygienic concerns.

BRIEF DESCRIPTION OF THE DRAWINGS

Without limiting the scope of the present invention as claimed below and referring now to the drawings and figures:

FIG. 3B shows a cross section view of a two compartment embodiment of the apparatus shown in FIG. 1 taken along section lines 2—2 of FIG 1;

FIG. 4B shows a cross section view of a two compartment embodiment of the apparatus shown in FIG. 1 taken along section lines 4—4 of FIG. 1;

FIG. 7 shows a cross section view of the apparatus shown in FIG. 1 taken along section lines 7—7 of FIG. 1;

FIG. 8 shows a top plan view of a variation of the frangible seal, enlarged;

FIG. 9 shows a top plan view of a variation of the frangible seal;

FIG. 10 shows a top plan view of yet another variation of the frangible seal;

FIG. 11 shows a top plan view of another variation of the frangible seal;

Figure 1:
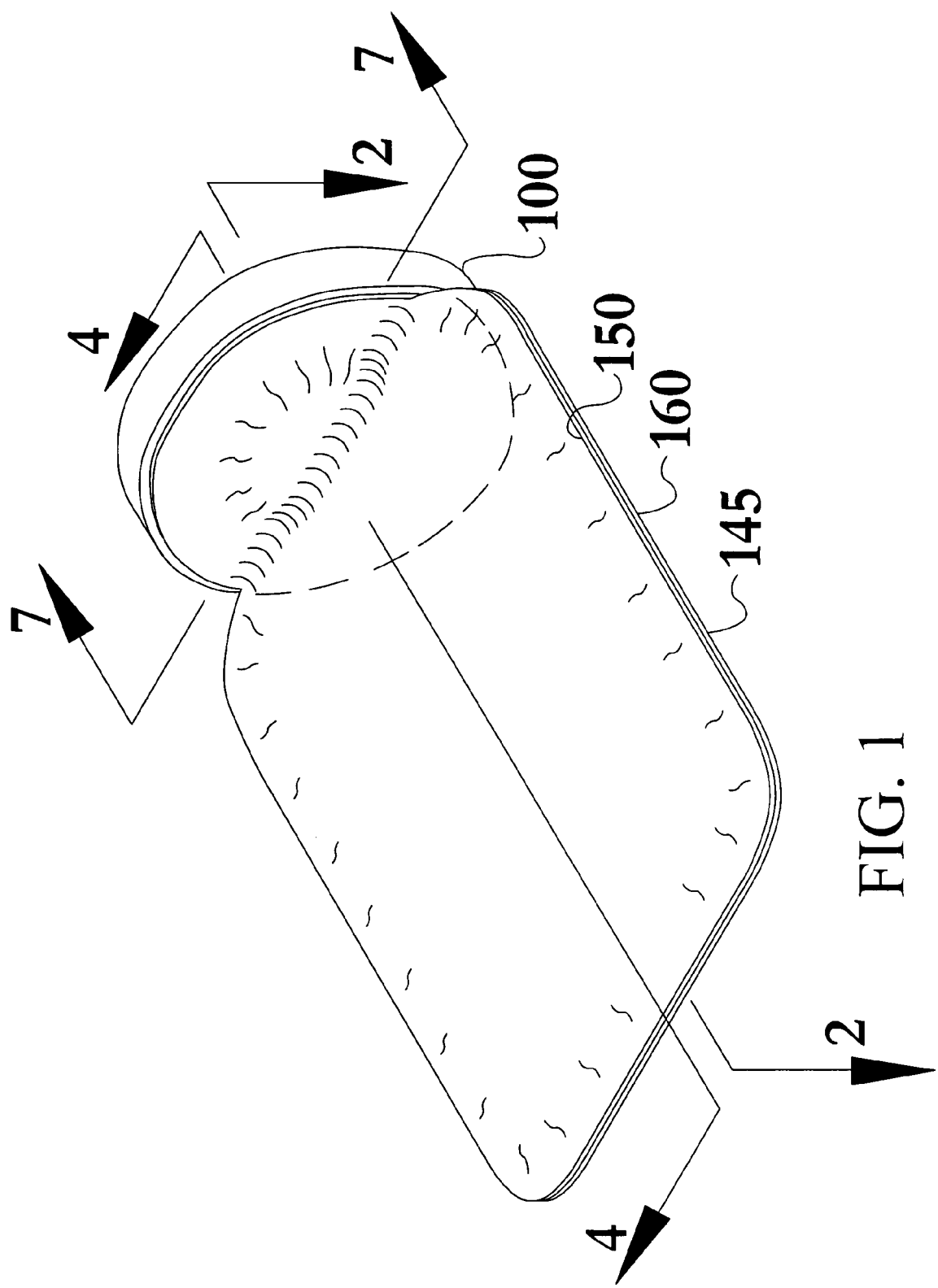
FIG. 1 shows a dispensing and application apparatus in elevated perspective view, in enlarged scale.

Also, in the various figures and drawings, the reference symbols "F" is used to identify an indication of flow.

Thus, this invention relates to a dispensing and application apparatus wherein the apparatus is designed to contain a flowable substance, comprising:

first and second compartments;

first and second frangible seals;

at least one sheet divided by at least one seal to form said first and second compartments;

an applicator having a periphery and being joined to the at least one sheet with at least one applicator bond;

a chamber being formed by the at least one sheet, and the applicator, and bounded in part by the applicator, the at least one applicator bond, and a frangible seal;

wherein said first frangible seal separates said first and second compartments and said second frangible seal separates said second compartment and said chamber; and, wherein said frangible seals are designed to break when exposed to a predetermined pressure, thereby creating a channel permitting fluid communication between said first compartment, said second compartment, said chamber and said applicator.

There is also disclosed a dispensing apparatus wherein the apparatus is designed to contain a flowable substance, comprising:

at least two compartments;

a first sheet section and a second sheet section interconnected with a primary seal and at least two frangible seals to form said compartments; the frangible seals being designed to break when exposed to a predetermined pressure thereby creating a channel permitting fluid communication between the compartments and a chamber;

an applicator having a periphery and being joined to the first sheet section and the second sheet section with at least one applicator bond; and the chamber being formed by the first sheet section, the second sheet section, and the applicator, and bounded in part by the applicator, the applicator bond, and one frangible seal.

There is further disclosed a dispensing, mixing and application apparatus wherein the apparatus is designed to separately contain a plurality of substances, comprising:

at least one sheet divided by a plurality of frangible seals to form a plurality of compartments including a first compartment housing a first substance and a second compartment housing a second substance;

a first frangible seal located at a common edge between the first compartment and a chamber, designed to break when exposed to a first predetermined pressure thereby creating a channel permitting communication between the first compartment and the chamber;

a second frangible seal located at an intermediate edge between the first compartment and the second compartment, designed to break when exposed to a second predetermined pressure, less than or equal to the first predetermined pressure, thereby creating a channel permitting communication between the first compartment and the second compartment permitting mixing of the first and second substances; and the chamber being formed by the at least one sheet and dispensing a mixture of at least the first and second substances.

DETAILED DESCRIPTION OF THE INVENTION

The storage and dispensing apparatus of the instant invention enables a significant advance in the state of the art. The preferred embodiments of the apparatus accomplish this by new and novel arrangements of elements that are configured in unique and novel ways and which demonstrate previously unavailable but preferred and desirable capabilities.

In one embodiment of the present invention, more than two compartments may be interconnected via frangible seals to ultimately communicate with the applicator. Such a dispensing apparatus is highly useful for multi-component mixtures wherein mixture just prior to use is highly desirable. Such a storage apparatus can increase shelf life, reduce degradation, and provide long-term storage capabilities of materials that are otherwise incompatible. Representative of such mixtures would be peptides in the presence of solvents, epoxies and amines for polymerization and easily hydrolyzed or solvent degraded materials.

This multi compartment system of the present invention provides for mixing of a solid, in powder or pellet form, with a liquid; or the mixing of a liquid with another liquid and also the mixing of two flowable powders.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

The storage and dispensing apparatus is designed to contain fluid substances, flowable dry products, and/or solid substances and to facilitate the dispensing of such contents. Referring generally to FIG. 1 through FIG. 13, the apparatus in its most general design comprises a compartment 130, a chamber 170, and at least one seal 148. Embodiments of the apparatus may incorporate multiple compartments 130A, 130B for separately housing contents, a dispensing conduit 194 for dispensing the contents, and an applicator 100 to apply the contents to a surface. The apparatus may be made, as would be apparent to one skilled in the art, of various flexible materials, including in at least one embodiment, a flexible laminated foil material. Other fabrication materials could include, by way of example and not limitation, various plastics, fabrics, and coated papers.

Figure 4A:
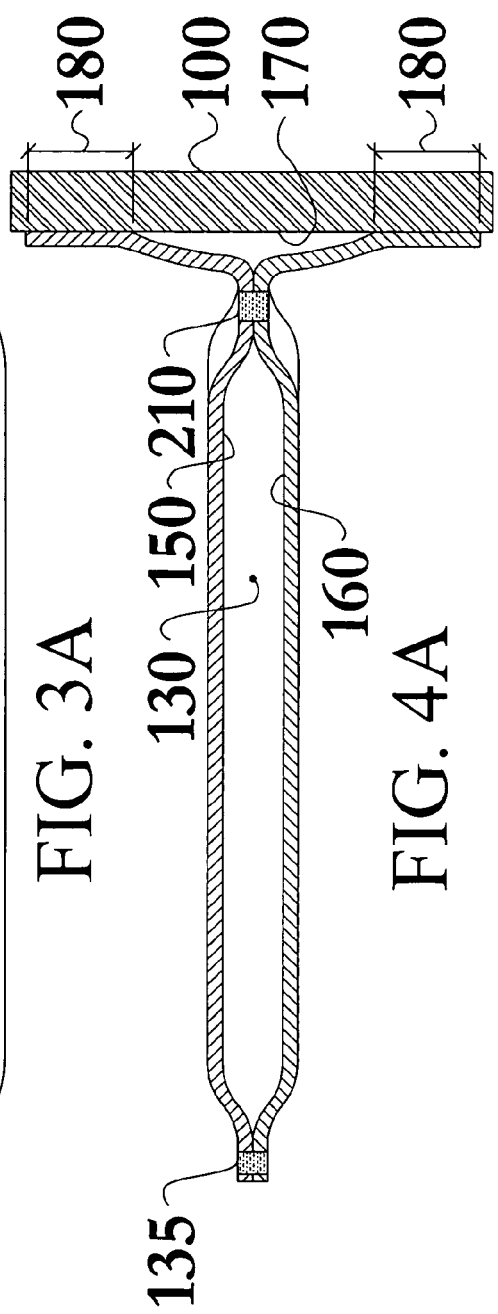
FIG. 4A shows a cross section view of an embodiment of the apparatus shown in FIG. 1 taken along section lines 4—4 of FIG. 1.
Figure 12:
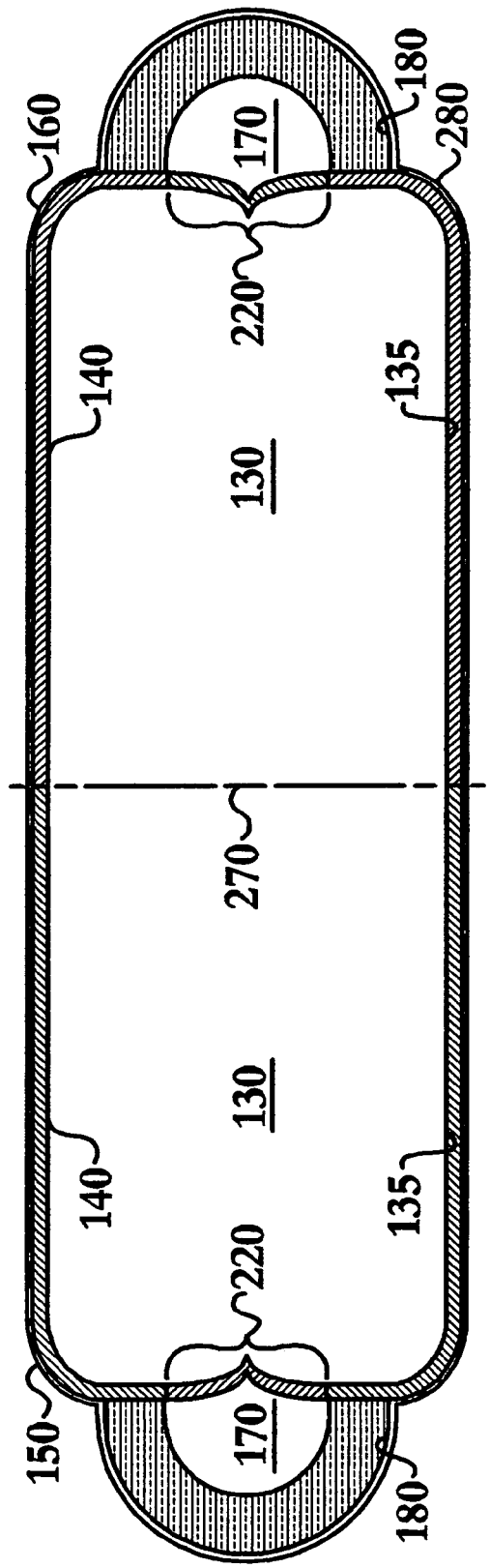
FIG. 12 shows a top plan view of a variation of the first and second sheet member of a single sheet embodiment, opened along a fold line and flattened out to a single plane, of the apparatus similar to that of FIG. 1.
Figure 13:
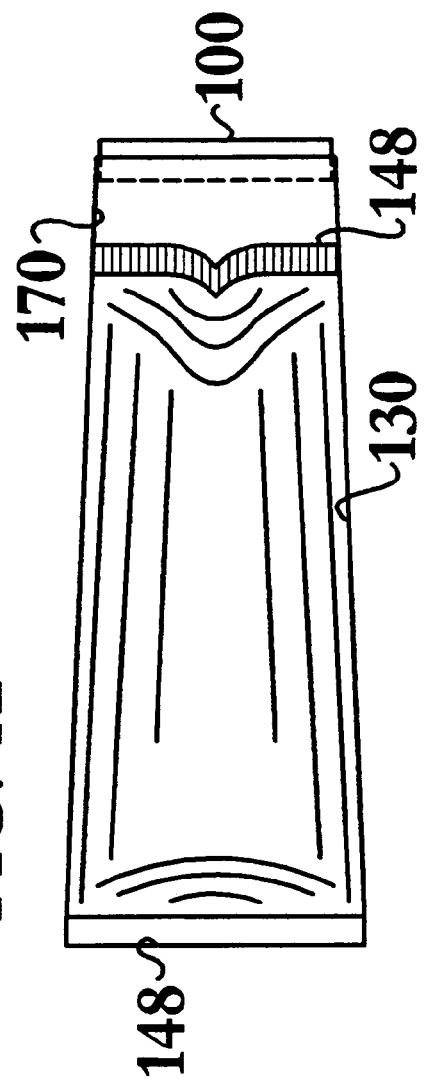
FIG. 13 shows a top plan view of the dispensing apparatus wherein the at least one sheet is configured as a tube.

The compartment 130 may be formed in part by at least one sheet 145 divided by at least one seal 148 to form the compartment. Alternatively, the compartment 130 can be formed with a first sheet section 150 and a second sheet section 160 interconnected with a primary seal 135, as shown in FIGS. 1 and 4A. Among other variations, the first sheet section 150 and second sheet section 160 can be formed from a single sheet 280 by folding the sheet 280 along a fold line 270, whereby the first sheet section 150 and second sheet section 160 are additionally interconnected at the fold line 270, as shown in FIG. 12. In yet another embodiment, the first sheet section 150 and a second sheet section 160, may be individual sheets, as shown in FIGS. 1, 4A, and 4B. In yet another embodiment, as shown in FIG. 13, the at least one sheet 145 may be configured as a tube with at least one seal 148. The design of the compartment 130 is intended to contain a measured amount of contents, ideally a single, or unit dose, under clean, or even sterile, conditions. In the embodiments where a primary seal 135 is used to fabricate the apparatus, the primary seal 135 is designed to reliably contain the contents at normal operating pressures during dispensing, as well as to provide a margin of safety to contain the contents in the event that the apparatus is briefly bumped, dropped, or otherwise transiently exposed to pressure.

Figure 2A:
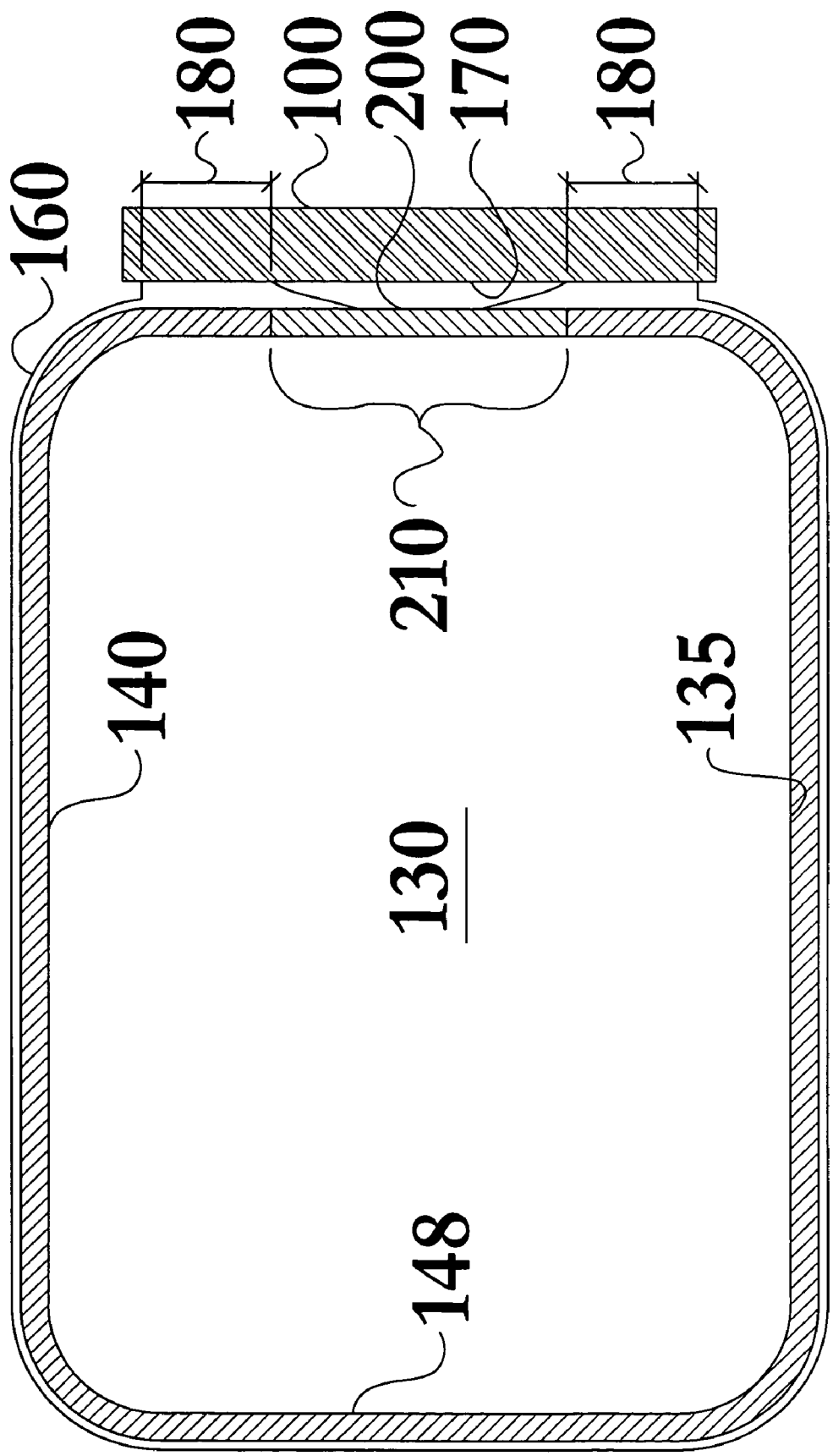
FIG. 2A shows a cross section view of the apparatus shown in FIG. 1 taken along section lines 2—2 of FIG. 1.
Figure 2B:
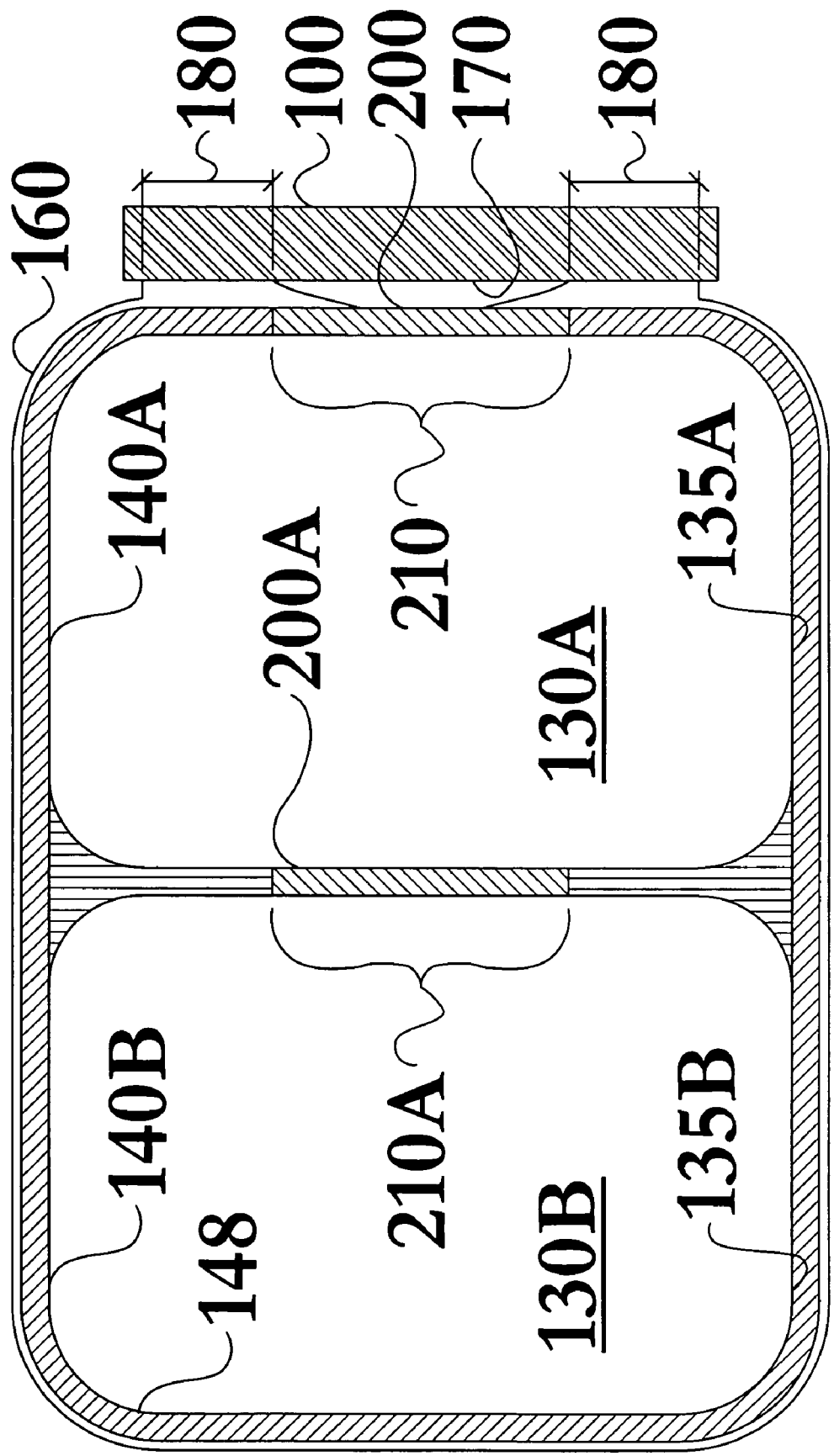
FIG. 2B shows a cross section view of a two compartment embodiment of the apparatus shown in FIG. 1 taken along section lines 2—2 of FIG. 1.

Further embodiments may incorporate multiple compartments 130A, 130B for separately housing various fluid substances, flowable dry products, and/or solid substances, as seen in FIGS. 2B, 3B, 3C, 4B, and 5B. As seen in FIG. 2B, a first compartment 130A and a second compartment 130B are divided by an intermediate edge 200A having a frangible seal 210A. Additionally, one with skill in the art can appreciate that the use of more than two compartments is contemplated by the present invention. The use of multiple compartments 130A, 130B to separately house various contents permits the contents of the individual compartments to be mixed prior to application. This is particularly beneficial for substances that either change form or may deteriorate after mixing. By way of example and not limitation, the first compartment 130A could hold a dissolvable tablet or powdered substance, while the second compartment 130B could hold a solvent. Rupturing the frangible seal between the compartments 210A would result in mixing, and the creation of a solute, still restrained within the container by the frangible seal 210 between the first compartment and the chamber 170. Similarly, substances that are activated by mixing, such as various two-part epoxy systems, could be stored, mixed, and dispensed with the inventive package.

Figure 5A:
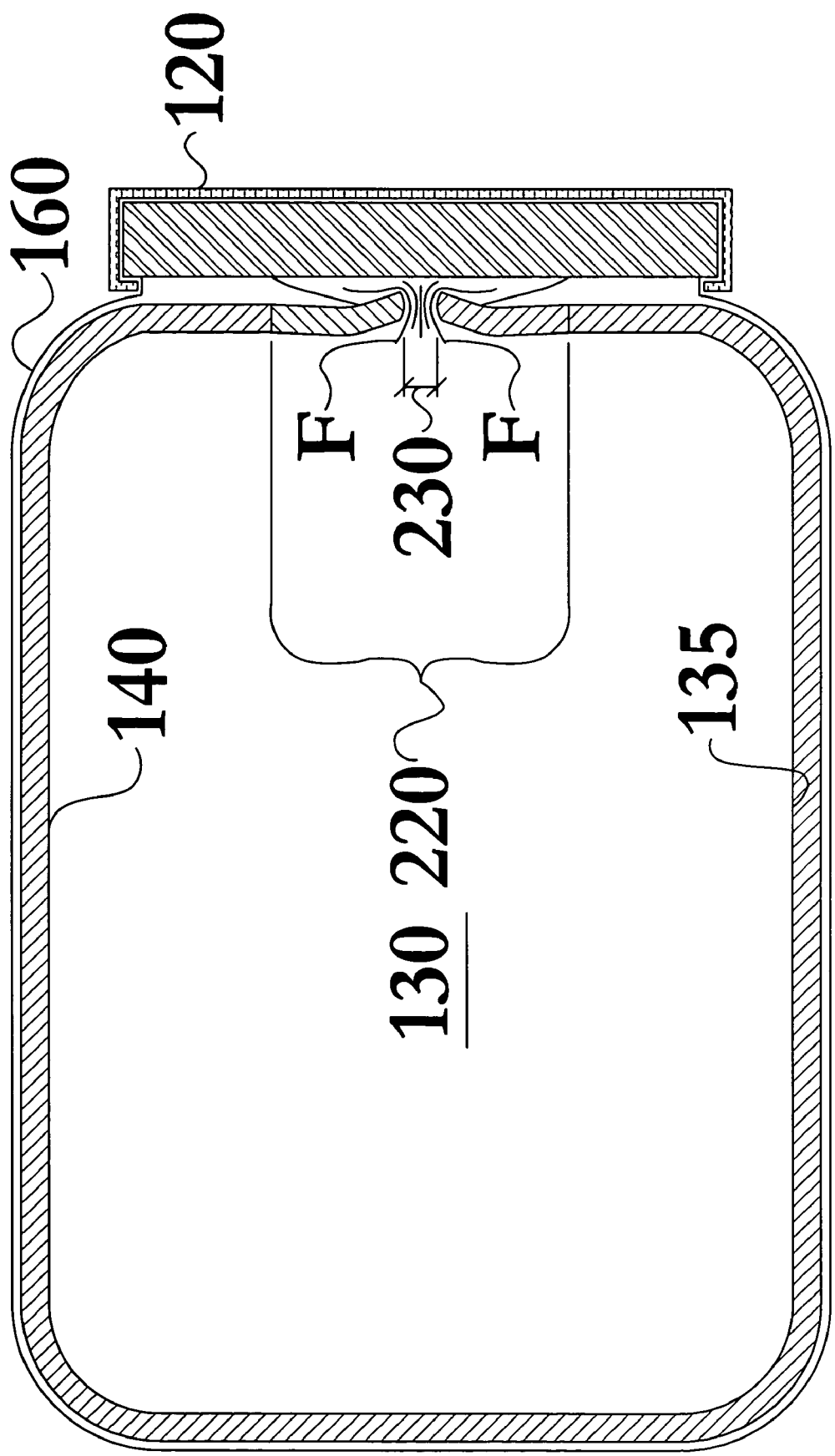
FIG. 5A shows a cross section view of a variation of the apparatus shown in FIG. 1 taken along section lines 2—2 of FIG. 1.
Figure 5B:
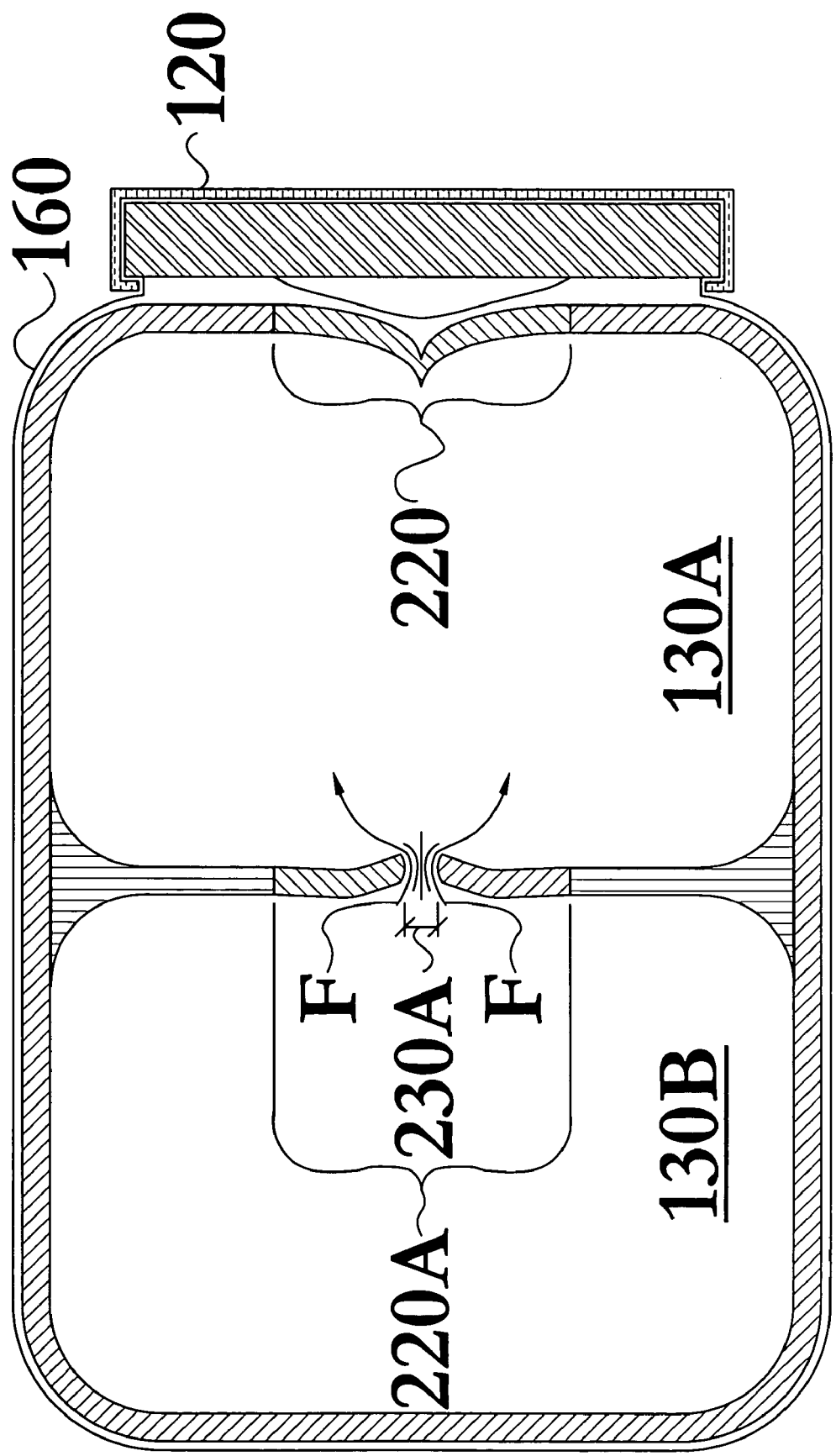
FIG. 5B shows a cross section view of a two compartment variation of the apparatus shown in FIG. 5A.

As seen in FIGS. 2A and 2B, at least one of the seals 148 is a frangible seal 210 designed to break when exposed to a predetermined pressure, creating a channel 230 permitting fluid communication between the compartment 130 and the chamber 170, as shown by flow indicator lines F in FIG. 5A. Similarly, in the multiple compartment embodiments, the intermediate edge 200A contains the frangible seal 210A, illustrated in FIG. 2B, between the compartments 130A and 130B so that the contents mix when the frangible seal 210A breaks, creating a channel 230A permitting communication between the compartments 130A and 130B, as illustrated in FIG. 5B. The frangible seals 210, 210A are particularly configured to have a lower rupture pressure than the primary seal 135. Additionally, the frangible seals 210, 210A are particularly configured to rupture in a controlled manner across a sufficient area to provide a relatively low pressure movement of contents into the chamber 170 or into an adjoining compartment 130A.

This controlled rupture property of the frangible seal 210, 210A is conferred by the design of the seal. The characteristics of the frangible seal 210 will be generally described herein with reference the to frangible seal 210 of the single compartment 130 embodiment, but such characteristics are equally applicable to the frangible seal 210A of the multiple compartment 130A, 130B embodiments. The frangible seal 210 may have a frangible seal first edge 212 and a frangible seal second edge 214, as indicated in FIG. 9, and multiple conformations are possible for the frangible seal 210, as indicated in FIGS. 2, 3, 8, 9, 10, and 11. In principles that are well known and apparent to those skilled in the art, the provision of an excursion, or excursions, on the surface of a seal, commonly known as stress risers 220 and inflection points 240, tends to create peel initiation points on the frangible seal 210, at which point or points the frangible seal 210 begins its opening response, or peel, in response to a pressure increase on the side of the frangible seal 210 in which the stress riser 220 or inflection point 240 is oriented. The developing pressure front of a pressure increase against a non-linear barrier, such as that of a seal with stress risers 220 or inflection points 240, is well known to have a region of maximum concentration of pressure in the region of maximum inflection of the stress riser 220, when the inflection point 240 is oriented to extend in the direction the compartment 130, 130A, 130B, that is, in the direction of the pressure front. This concentration of force of the pressure front tends to preferentially initiate seal opening, or peel, at the stress riser 220.

It is not necessary that the stress riser 220 have any particular configuration, only, as is well known in the art, the initiation of seal opening, or peel, is enhanced as the inflection point 240 of a stress riser 220 becomes sharper. Thus, a gently curved frangible seal 210, 210A as seen in FIG. 8, would tend to concentrate force at a particular point less intensely than would a frangible seal 210, 210A having a stress riser 220 or inflection point 240 that resembled a sharp saw tooth, as seen in FIG. 11.

Figure 3A:
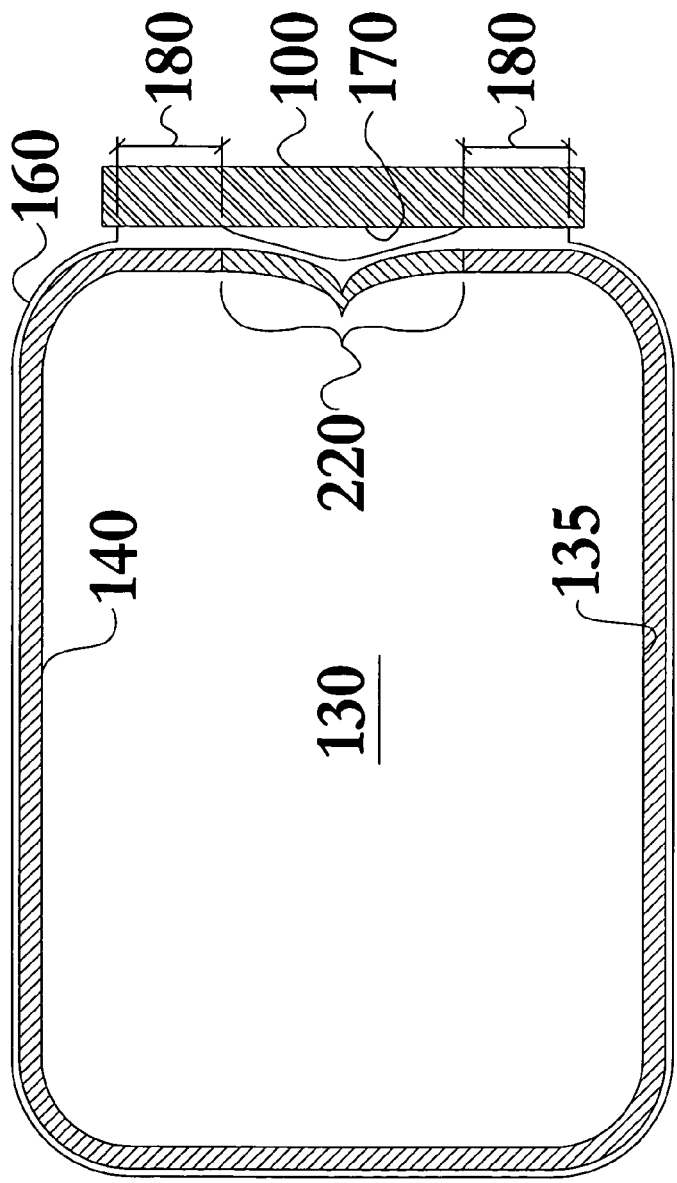
FIG. 3A shows a cross section view of a variation of the embodiment of the apparatus shown in FIG. 1 taken along section lines 2—2 of FIG. 1.
Figure 3C:
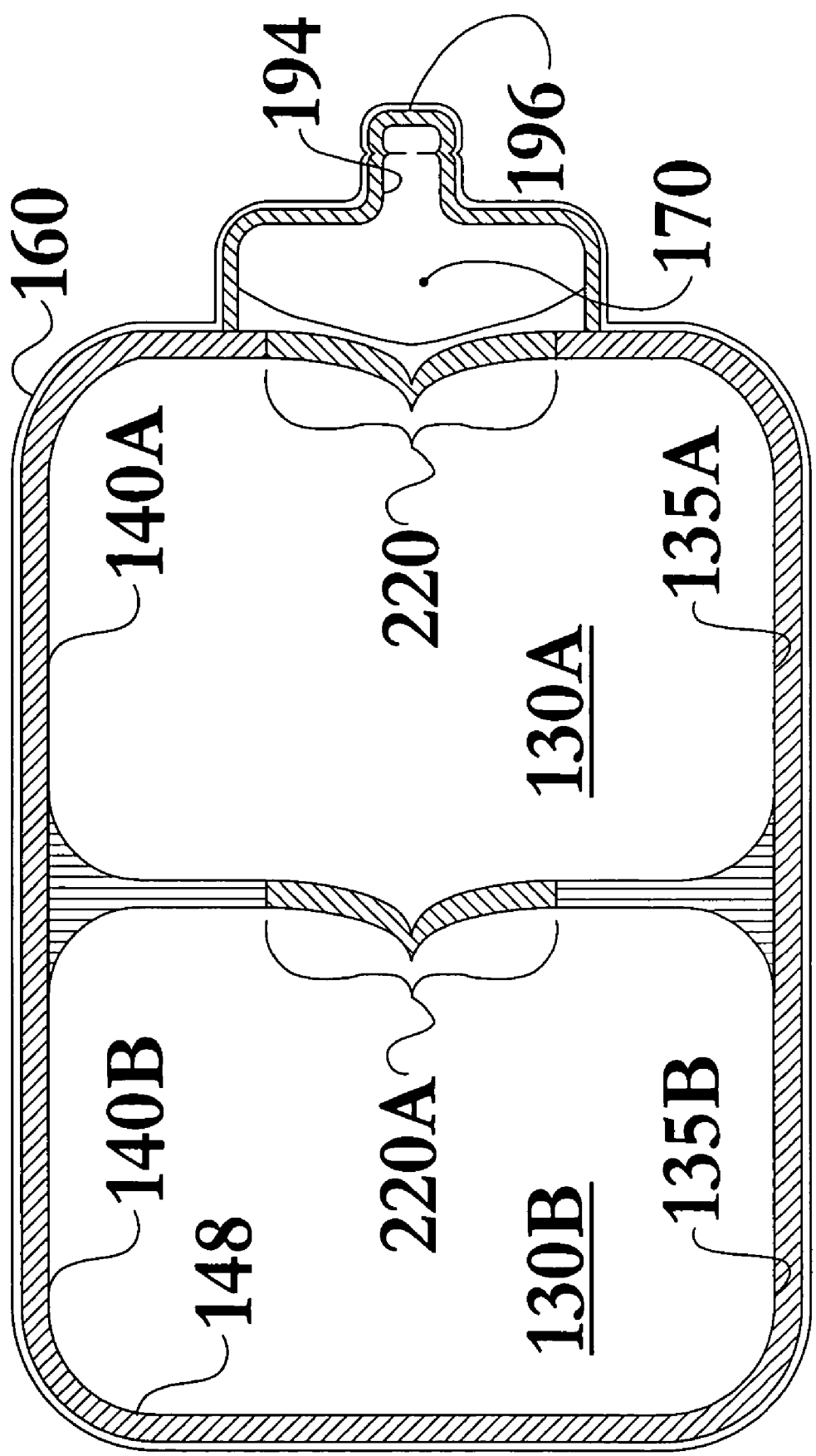
FIG. 3C shows a cross section view of a variation of the two compartment embodiment of the apparatus shown in FIG. 3B.
Figure 6:
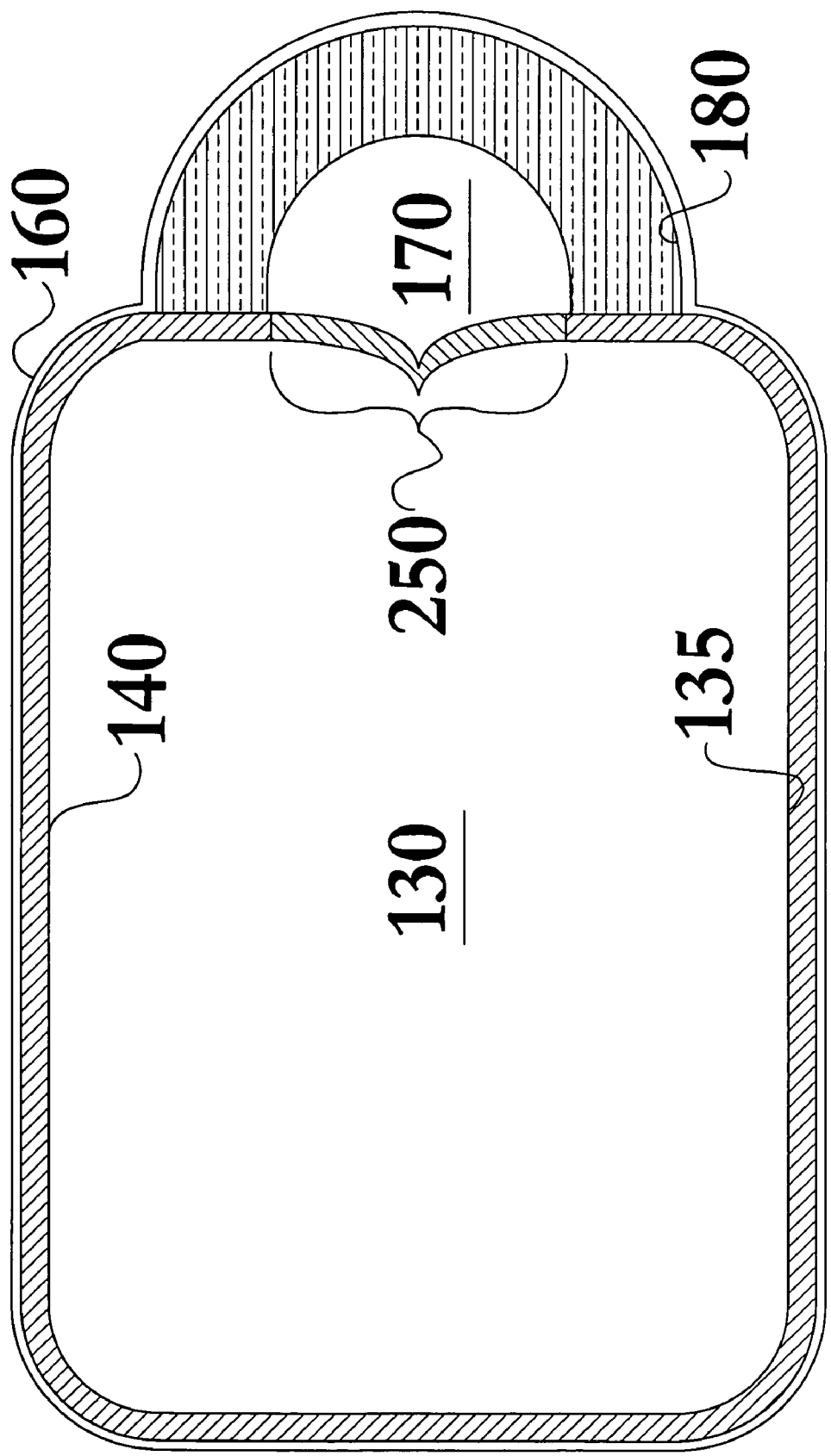
FIG. 6 shows a top plan view of a variation of the second surface (interior surface), flattened out to a single plane, of the apparatus shown in FIG. 1.

In its simplest construction, the frangible seal 210, 210A may be flat, as seen in FIGS. 2A and 2B, which represents the apparatus as though the first sheet section 150 had been peeled away (in cross section taken through line 2—2), leaving the second sheet section 160 exposed for better viewing. In one embodiment of the instant invention, shown in FIG. 8, the stress riser 220 of the frangible seal 210 is formed to have at least one sinusoidal shape. This, as discussed, would be a design that would generally be relatively more difficult to rupture than for example FIG. 11. In another embodiment, the frangible seal 210 further includes a stress riser 220 as seen in FIGS. 3A, 3B, and 3C. Such a stress riser 220, as discussed, would make the frangible seal 210 generally easier to rupture than for example FIG. 11. A stress riser 220 may have different configurations in different embodiments, which include, among others, a substantially chevron shape 250, as shown in FIG. 6, which represents the apparatus as though the first sheet section 150 had been peeled away, leaving the second sheet section 160 exposed, with the second sheet section 160 flattened out for better viewing. The chevron shape stress riser 250 may have a sharp inflection point 260, seen in FIG. 9, oriented in the direction of the compartment 130.

Additionally, in those embodiments utilizing a frangible seal 210 with a chevron shaped stress riser 250 oriented with the point of maximum inflection 240 of the frangible seal first edge 212 being towards the compartment 130. The chevron shape stress riser 250 may have a rear chevron inflection point 260 whereby a maximum orthogonal distance from the rear chevron inflection point 260 to the frangible seal second edge 214 is less than a maximum orthogonal distance between the frangible seal first edge 212 and the frangible seal second edge 214, as shown in FIG. 9. This embodiment has been shown to provide optimal performance in terms of strength and rupture characteristics.

The selection of an optimal design of the stress riser or risers, would lie within the skill of one with ordinary skill in the art, and might be selected to reflect particular characteristics of the substance to be dispensed, including by way of example and not limitation, viscosity, or flowability, of the dispensed substance, desired rupture resistance characteristics of the packaging, type and size of applicator 100, and size of chamber 170. The primary seal 135 and frangible seal 210 may be formed by a variety of techniques, as would be apparent to one skilled in the art, including but not limited to thermal seals, and mechanical or chemical seals. Such mechanical seals could include, by way of example and not limitation, crimping and various retainer clips; and such thermal or chemical seals could include, by way of example and not limitation, adhesive bonds such as chemical adhesive or hot melt techniques, or other fusion methods.

The chamber 170 may further include a dispensing conduit 194 for discharging the contents of the apparatus, as illustrated in FIG. 3C. Additionally, the dispensing conduit 194 may terminate with a removable conduit end cap 196 to keep contaminants from entering the apparatus. In this embodiment, the chamber 170 may have a volume significantly greater than that of the dispensing conduit 194, as seen in FIG. 3C, or the chamber 170 and the dispensing conduit 194 may be the same size and shape so that they are indistinguishable from one another.

Alternatively, many uses of the inventive apparatus have the additional need of an applicator. As previously discussed, a severe shortcoming of the prior art has been the lack of a well functioning applicator 100 in dispensing packages. For optimal function, an applicator 100 needs to be absorbent, to facilitate the spreading of dispensed substance within the applicator 100, and to allow the user to apply the dispensed substance easily, and in those applications to the skin, comfortably and cleanly. In one embodiment, the instant invention achieves these goals as the apparatus is further configured with an applicator 100, which has a periphery 110 and is joined to the at least one sheet 145 with at least one applicator bond 180, best illustrated in FIG. 6. The applicator 100 may be a substantially porous absorbent pad, for example a foam pad. As seen in FIG. 7, the applicator bond 180 is formed with an interior edge 190 and an exterior edge 192 and in a preferred embodiment the exterior edge 192, is within the applicator periphery 110. Additionally, the at least one applicator bond 180 may be a chemical and mechanical bond between the applicator 100 and the at least one sheet 145. Such mechanical bonds could include, by way of example and not limitation, crimping and various retainer clips; and such thermal or chemical bonds could include, by way of example and not limitation, adhesive bonds such as chemical adhesive or hot melt techniques, or other fusion methods.

The embodiment utilizing a configuration wherein the applicator bond 180 lies within the applicator periphery 110, seen in FIG. 7, confers particular advantages on the apparatus. As the applicator bond 180 tends to restrict the flow of the dispensed substance to that area inside the applicator bond interior edge 190, having a portion of the applicator 100 lying outside of the applicator bond area 180 initially provides for an area of dry surface that facilitates an even and comfortable spreading of the dispensed substance. Additionally, this results in a relatively soft edge portion for the applicator 100, which increases comfort levels when the applicator 100 is used to spread a substance on the skin.

Besides the need for an applicator 100 for optimal dispensing, experiments with various means of attachment of the applicator 100 to a dispensing package indicated that a key design feature necessary to proper function is the provision of a relatively expansive area that may receive the dispensed substance, as it is being dispensed at relatively high pressure and velocity through the rupturing frangible seal 210. Such a relatively expandable area allows the dispensed substance to spread out and dissipate the energy it had when passing at a relatively high velocity through the channel 230 and into the chamber 170 so it can be gently spread into an applicator. In the absence of such an expandable area, or if the expandable area is too small or otherwise insufficiently expandable, the relatively high pressure of the dispensed substance tends to shoot through or past the applicator 100, without spreading out into the applicator 100. On the other hand, if the expandable area is too large, or otherwise excessively expandable, it is possible for the dispensed substance to achieve such a low pressure state that it does not adequately spread into the applicator 100.

Accordingly, an optimal design should provide for an easy means of fabricating packages with varying sized expandable areas. The instant invention accomplishes this by its utilization of a chamber 170, and an applicator bond area 180 and applicator 100, and in particular, expandability is imparted to the chamber by the expansion of the chamber 170 walls and by the resilient nature of the applicator 100. This resilient nature allows the contents of the chamber 170 to expand under pressure, thereby absorbing the hydraulic shock as the dispensed substance breaks through the frangible seal 210 and enters the chamber 170. The dispensed substance then tends to remain behind the applicator 100 and can be easily dispensed and spread when the applicator 100 is pressed against a surface.

The volume of the chamber 170 may be varied by varying the relative size of the at least one applicator bond area 180 and the applicator 100. In a preferred embodiment, the surface area of the bond area 180 is between approximately 62.5% of the surface area of the applicator 100 and approximately 87.5% of the surface area of the applicator 100. As the ratio of the area of the applicator bond area 180 to the area of the applicator 100, expressed as a percentage, increases towards 100%, the expandability of the chamber 170 decreases and the high pressure and velocity effects noted above would become more prominent. As the ratio of the area of the applicator bond area 180 to the area of the applicator 100, expressed as a percentage, decreases towards zero, a point which it cannot reach due to the necessary resulting failure of the bond, the expandability of the chamber 170 increases and the low pressure effects noted above would become more prominent. Numerous embodiments are possible, as would be apparent to one skilled in the art, varying this applicator bond area 180 to applicator 100 area relationships, and might be selected to reflect particular characteristics of the substance to be dispensed, including by way of example and not limitation, viscosity of the dispensed substance.

The chamber 170 may be formed by the at least one sheet 145, and the applicator 100, and may be bounded in part by the applicator 100, the at least one applicator bond 180, and the frangible seal 210. In an alternate embodiment, the chamber 170 may be additionally bounded in part by one of the at least one seals 148. Alternatively, such as is shown in FIG. 4A, in embodiments where the compartment 130 is formed with a first sheet section 150 and a second sheet section 160 interconnected with a primary seal 135, the chamber 170 may be formed by the first sheet section 150, the second sheet section 160, and the applicator 100, and bounded in part by the applicator 100, the applicator bond 180, and the frangible seal 210. The chamber 170 may additionally be bounded in part by the primary seal 135.

To protect the contents and to promote cleanliness of the device, the apparatus may include an applicator cover 120 adapted to releasably enclose the applicator, as shown in FIGS. 5A and 5B. Additionally or alternately, as would be apparent to one skilled in the art, the entire apparatus could be enclosed in a suitable packaging to maintain cleanliness, or even in a special use packaging to keep the apparatus sterile. The preferred embodiment of the apparatus is that of a relatively small, hand held device, but there are no particular restrictions on the size of the apparatus or the amount of substance that might be dispensed, other than those general considerations of size, weight, and resultant ease of use.

These variations, modifications, alternatives, and alterations of the various preferred embodiments, arrangements, and configurations may be used alone or in combination with one another as will become more readily apparent to those with skill in the art with reference to the following detailed description of the preferred embodiments and the accompanying figures and drawings.

INDUSTRIAL APPLICABILITY

The apparatus answers a long felt need for a low cost disposable packaging for a wide array of substances, which can include, by way of example and not limitation; pharmaceutical antiseptics, salves, ointments, creams, powders, solutions, and multi-part solutions. The apparatus provides a packaging that offers convenience in storage, resistance to package breakage, better sanitation, and lower spillage or waste. Additionally, the apparatus provides a packaging that allows a user to apply a small measured quantity of a substance in a controlled manner without getting it on the fingers or hands and without the necessity of using the fingers, hands or an additional implement to spread the substance. The apparatus allows multi-part solutions to be separately stored and yet effectively mixed just prior to use.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations.

Accordingly, even though only few variations of the present invention are described herein, it is to be understood that the practice of such additional modifications and variations and the equivalents thereof, are within the spirit and scope of the invention as defined in the following claims.

We claim:

1. A dispensing and application apparatus wherein the apparatus is designed to contain a flowable substance, comprising:
   first and second compartments;
   first and second frangible seals;
   at least one sheet divided by at least one seal to form said first and second compartments;
   an applicator having a periphery and being joined to the at least one sheet with at least one applicator bond;
   an expansible chamber being formed by the at least one sheet, and the applicator, and bounded in part by the applicator, the at least one applicator bond, and the second frangible seal such that the expansible chamber absorbs a portion of the kinetic energy of the flowable substance after it breaks through the second frangible seal;

wherein said first frangible seal separates said first and second compartments and said second frangible seal separates said second compartment and said expansible chamber; and, wherein said first frangible seal further includes a first stress riser oriented in the direction of the first compartment and is designed to break when exposed to a first predetermined pressure internal to the compartment, created by externally pinching the first compartment, where the first frangible seal peels apart in such a manner that no portion of the frangible seal separates from the at least one sheet and becomes entrained in the flowable substance, thereby creating a channel permitting fluid communication between said first compartment and said second compartment and said second frangible seal further includes a second stress riser oriented in the direction of the second compartment and is designed to break when exposed to a second predetermined pressure, internal to the compartment, created by externally pinching the second compartment, where the second frangible seal peels apart in such a manner that no portion of the frangible seal separates from the at least one sheet and becomes entrained in the flowable substance, thereby creating a channel permitting fluid communication between at least said second compartment, said chamber and said applicator.

2. The apparatus of claim 1, wherein said stress risers are formed of at least one sharp inflection point.

3. The apparatus of claim 2, wherein said stress risers formed of at least one sharp inflection point further comprise a substantially chevron shape having a sharp inflection point oriented in the direction of said first and second compartments.

4. The apparatus of claim 3, wherein at least one of said frangible seals is formed to include a frangible seal first edge and a frangible seal second edge, and the substantially chevron shape has a rear chevron inflection point whereby a maximum orthogonal distance from the rear inflection point to the frangible seal second edge is less than a maximum orthogonal distance between the frangible seal first edge and the frangible seal second edge.

5. The apparatus of claim 1, wherein the applicator comprises a porous absorbent pad.

6. The apparatus of claim 1, wherein said applicator is a foam pad.

7. The apparatus of claim 1, wherein said at least one sheet comprises a flexible laminated foil.

8. The apparatus of claim 1, wherein the surface area of the bond area is between 62.5% and 87.5% of the surface area of the applicator.

9. The apparatus of claim 1, further comprising an applicator cover adapted to releasably enclose the applicator.

10. The apparatus of claim 1, wherein said at least one seal and said frangible seals are thermal seals.

11. A dispensing and application apparatus wherein the apparatus is designed to contain a flowable substance, comprising:

at least two compartments;

a first sheet section and a second sheet section interconnected with a primary seal and at least two frangible seals to form said compartments, the frangible seals further including stress risers oriented in the direction of the compartments and being designed to break when exposed to a predetermined pressure internal to the compartments, created by externally pinching the compartments, where the frangible seals peel apart in such a manner that no portion of the frangible seals separates from the at least one sheet and becomes entrained in the flowable substance, thereby creating a channel permitting fluid communication between the compartments and an expansible chamber;

an applicator having a periphery and being joined to the first sheet section and the second sheet section with at least one applicator bond; and the expansible chamber being formed by the first sheet section, the second sheet section, and the applicator, and bounded in part by the applicator, the applicator bond, and one frangible seal.

12. The apparatus of claim 11, wherein the first sheet section and the second sheet section are formed from a single sheet by folding the sheet along a fold line, whereby the first sheet section and second sheet section are additionally interconnected at the fold line.

13. The apparatus of claim 11, wherein said stress risers are formed of at least one sharp inflection point.

14. The apparatus of claim 13, wherein said stress risers formed of at least one sharp inflection point further comprise a substantially chevron shape having a sharp inflection point oriented in the direction of said compartment.

15. The apparatus of claim 11, wherein said first sheet section and said second sheet section comprise flexible laminated foil.

16. The apparatus of claim 11, wherein the surface area of the bond area is between 62.5% and 87.5% of the surface area of the applicator.

17. The apparatus of claim 11, further comprising an applicator cover adapted to releasably enclose the applicator.

18. The apparatus of claim 11, wherein said primary seal and said frangible seal are thermal seals.

19. A dispensing, mixing, and application apparatus wherein the apparatus is designed to separately contain a plurality of substances, comprising:

at least one sheet divided by a plurality of frangible seals to form a plurality of compartments including a first compartment housing a first substance and a second compartment housing a second substance;

a first frangible seal located at an intermediate edge between the first compartment and the second compartment, further including a first stress riser oriented in the direction of the first compartment and designed to break when exposed to a first predetermined pressure, internal to the compartment, created by externally pinching the first compartment, where the first frangible seal peels apart in such a manner that no portion of the frangible seal separates from the at least one sheet and becomes entrained in the flowable substance, less than or equal to a second predetermined pressure, thereby creating a channel permitting communication between the first compartment and the second compartment permitting mixing of the first and second substances;

a second frangible seal located at a common edge between the second compartment and a chamber, further including a second stress riser oriented in the direction of the second compartment and designed to break when exposed to a second predetermined pressure internal to the compartment, created by externally pinching the second compartment, where the second frangible seal peels apart in such a manner that no portion of the frangible seal separates from the at least one sheet and becomes entrained in the flowable substance, thereby creating a channel permitting communication between the second compartment and an expansible chamber; and the expansible chamber being formed by the at least one sheet such that the expansible chamber absorbs a portion of the kinetic energy of the flowable substance after it breaks through the second frangible seal, and dispensing a mixture of at least the first and second substances.

20. The apparatus of claim 19, further including an applicator having a periphery and being joined to the at least one sheet with at least one applicator bond so that the chamber is bounded in part by the applicator, the at least one applicator bond, and the second frangible seal.

21. The apparatus of claim 20, wherein the applicator comprises a porous absorbent pad.

22. The apparatus of claim 21, wherein the applicator is a foam pad.

23. The apparatus of claim 20, wherein the applicator bond exterior edge is within the applicator periphery.

24. The apparatus of claim 20, wherein the surface area of the bond area is between 62.5% and 87.5% of the surface area of the applicator.

25. The apparatus of claim 19, wherein the chamber has a dispensing conduit having a removable conduit end cap so that the dispensing conduit may transmit the mixture of the first and second substances to a dispensing point when the removable conduit end cap is removed.

26. The apparatus of claim 19, wherein the at least one sheet includes a first sheet section and a second sheet section.

27. The apparatus of claim 26, wherein the first sheet section and the second sheet section are formed from a single sheet by folding the sheet along a fold line.

28. The apparatus of claim 19, wherein stress risers are formed of at least one sharp inflection point.

29. The apparatus of claim 28, wherein each stress riser formed of at least one sharp inflection point further comprises a chevron shape having a sharp inflection point oriented in the direction of the associated compartment.

30. The apparatus of claim 29, wherein each frangible seal is formed to include a frangible seal first edge and a frangible seal second edge, and the chevron shape has a rear chevron inflection point whereby a maximum orthogonal distance from the rear inflection point to the frangible seal second edge is less than a maximum orthogonal distance between the frangible seal first edge and the frangible seal second edge.

31. The apparatus of claim 19, wherein the at least one sheet comprises a flexible laminated foil material.

32. The apparatus of claim 19, wherein the at least one seal and the frangible seals are thermal seals.

* * * * *